United States Patent [19]
Tung et al.

[11] Patent Number: 5,902,912
[45] Date of Patent: May 11, 1999

[54] PROCESS FOR PREPARING HYDROFLUOROCARBONS

[75] Inventors: Hsueh Sung Tung, Getzville; Daniel Christopher Merkel, West Seneca; Addison Miles Smith, Amherst, all of N.Y.

[73] Assignee: AlliedSignal Inc., Morristown, N.J.

[21] Appl. No.: 08/882,805

[22] Filed: Jun. 26, 1997

[51] Int. Cl.⁶ .................................................. C07C 17/08
[52] U.S. Cl. ........................ 570/164; 570/165; 570/166; 570/167; 570/168
[58] Field of Search ................................ 570/165, 166, 570/167, 168, 169, 164

[56] References Cited

FOREIGN PATENT DOCUMENTS

WO95/35271  12/1995  Germany .
233 102     9/1995   Japan .

*Primary Examiner*—Alan Siegel
*Attorney, Agent, or Firm*—Jay P. Friedenson; Colleen D. Szuch

[57] ABSTRACT

A process for producing a hydrofluorocarbon (HFC) comprising (a) providing a fluoropolymer-lined reactor; (b) adding a chlorinated organic compound in liquid phase and a fluorination agent to the reactor; and (c) reacting at least a portion of the chlorinated organic compound with at least a portion of the fluorination agent to produce the HFC.

8 Claims, No Drawings

PROCESS FOR PREPARING HYDROFLUOROCARBONS

FIELD OF INVENTION

The present invention relates generally to the preparation of hydrofluorocarbons (HFCs). More specifically, this invention relates to a fluorination process that minimizes reactor corrosion and improves the yield and purity of the HFCs produced.

BACKGROUND OF THE INVENTION

Because hydrofluorocarbons (HFCs) do not deplete the ozone layer, they are becoming popular substitutes for chlorofluorocarbons (CFCs) and hydrochlorofluorocarbons (HCFCs) for use as heat transfer agents, blowing agents, and propellants. HFCs are typically prepared by fluorinating a chlorinated organic compound with a fluorination agent such as hydrogen fluoride in the presence of a fluorination catalyst. This reaction may be conducted in either the liquid or gas phase. Generally, the liquid phase fluorination is preferred because the reaction is controlled at relatively lower temperatures which results in less by-product formation due to decomposition.

Liquid phase fluorination, however, uses and generates corrosive compounds, such as, for example, hydrogen fluoride, hydrogen chloride, and catalysts, which form superacids. These superacids tend to corrode the reactor in which the reaction is conducted, even reactors comprised of corrosion-resistant materials such as Inconel 600, NAR25-50MII, Hastelloy C, Hastelloy G-30, duplex stainless steel, and Hastelloy C-22. Corrosion of the reactor compromises the structural integrity of the reactor and reduces its useful life. Therefore, a need to minimize reactor corrosion exists.

One method of reducing such corrosion is taught in Japanese Kokai Patent Application Publication No. 233102 (1995). In this publication, a method is disclosed for the liquid phase fluorination of a chlorinated organic compound in a reactor made or lined with a fluorine resin. The method involves gaseous feeds of hydrogen fluoride and chlorinated organic compound. Because the process is restricted to gaseous feed streams, it is limited in the type of HFCs it can produce. Chlorinated organic compounds having two or more carbon atoms tend to decompose before reaching their gaseous state. For example, pentachloropropane tends to decompose significantly at temperature greater than 90° C. while its boiling point is about 190° C. Thus, as a practical matter, the process disclosed in this publication can only be used to produce fluorinated methanes.

The aforementioned Japanese publication also states that when heat transfer through the reactor is necessary, which is usually the case in liquid phase fluorination, the fluorine resin liner should be applied using a molding method. The only molding method identified therein is rotary-baked molding.

Generally, reactors having a molded liner, such as a rotary-baked or sprayed-on liner, are not suitable for large-scale commercial production. Reactors having such liners must be baked in large kilns or ovens, which are expensive and frequently unavailable. Indeed, fitting a large reactor, for example, greater than about a 1,000 gallons, with a baked liner is impractical.

A molded liner not only imposes practical limitations on the reactor, but also introduces structural limitations. It has been found that molded liners tend to be permeable and, under high pressures and over time, reactants tend to penetrate the liner and develop pressure between the liner and the reactor wall. This pressure causes the liner to blister, and eventually the liner comes loose. The problem of liner penetration is exacerbated by the absence of weep holes in a molded-liner reactor. Ordinarily, weep holes allow reactants that penetrate the liner to escape from the reactor. A molded liner, however, generally cannot be used in a reactor with weep holes. When applying a molded liner, a fluid fluoropolymer is applied to the reactor wall, and, thus, holes in the reactor wall will result in holes in the molded liner. Holes in the liner obviously compromise the reactor's ability to be pressurized. Therefore, while a rotary-baked, fluorine-resin liner may minimize reactor corrosion, its structural limitations nevertheless limit the reactor's useful life.

Therefore, a need exists for a commercially viable method of producing a wide range of HFCs while minimizing reactor corrosion. The present invention fulfills this need among others.

DESCRIPTION OF THE INVENTION AND PREFERRED EMBODIMENTS

The present invention is directed to a fluorination process which uses a commercially viable and durable fluoropolymer-lined reactor, as described hereafter, to produce a wide variety of hydrofluorocarbons (HFCs), including those having two or more carbon atoms.

In one embodiment, the process comprises: (a) providing reactor means for effecting fluorination in which at least a portion of the reactor means is fluoropolymer-lined; (b) adding a fluorination agent and a liquid chlorinated organic compound to the reactor means; and (c) reacting in the liquid phase at least a portion of the starting materials to produce a HFC. Since this embodiment adds the chlorinated organic compound to the reactor in liquid phase rather than gas phase, compounds having two or more carbon atoms can be used without decomposing.

Another embodiment of the process comprises: (a) providing a reactor with a loose, fluoropolymer liner; and (b) reacting at least a portion of a chlorinated organic compound with at least a portion of a fluorination agent in the reactor to produce an HFC. A loose, fluoropolymer liner, as described hereafter, provides a reactor with a chemically-resistant barrier that is more durable then molded-type, fluoropolymer liners. More specifically, a loose liner tends to be less porous than a molded liner and, thus, tends to maintain a seal for a longer time.

Yet another embodiment of the process comprises: (a) providing a fluoropolymer-lined reactor having weep holes; and (b) reacting at least a portion of a chlorinated organic compound with at least a portion of a fluorination agent in the reactor to produce an HFC. The weep-holes allow those reactants that permeate the fluoropolymer-lined reactor to be vented or otherwise removed. This prevents reactants from building up pressure between the liner and the reactor wall and forming blisters in the liner.

In a preferred embodiment, the process comprises a combination of the above embodiments.

An important aspect of the present invention is the use of a fluoropolymer liner on at least a portion of the reactor means. As used herein, the terms "fluorinated polymer" and "fluoropolymer" are used synonymously and broadly refer to any polymer, copolymer or blend of polymers having a fluoride atom in at least one of the monomers. Preferred materials include, for example, polytetrafluoroethylene, poly(vinylidene fluoride), ethylene-tetrafluoroethylene polymer, ethylene-hexafluoropropylene polymer, tetrafluoroethylene-hexafluoropropylene polymer, any modified version of the above-mentioned polymers, and blends of two or more thereof. The polytetrafluoroethylene liner or its modified version is more preferred.

The reactor means for facilitating fluorination may comprise any apparatus conventionally used for preparing HFCs by liquid phase fluorination. An example of a satisfactory apparatus for this purpose is one consisting of a single reaction vessel, such as an autoclave, to which the starting materials can be added, in liquid or gaseous form, and heated or cooled well enough to keep the reaction temperature at a set temperature. The reaction vessel should promote contact among the reactants by a suitable mixing method and be capable of sustaining reaction pressures up to about 300 psi or whatever the maximum reaction pressure is expected to be. Because the reaction typically takes place under pressure, the reactor vessel is generally comprised of metal or other structurally rigid material. Suitable materials include, for example, carbon steel, stainless steel, Inconel alloy, Monel alloy, Hastelloy, or other type of a structurally suitable alloy.

In the preferred embodiment, the reactor wall has at least one weep hole, and preferably a plurality of weep holes. Weep holes allow reactants that permeate the liner to be vented or otherwise removed from between the liner and the reactor wall. The number and size of the weep holes may vary according to reactor size and other variables, although a weep hole having a diameter from about ⅛ to about ½ inch is generally preferred. A reactor having one or more weep holes requires that the liner have adequate strength to span the weep hole under reaction pressures.

The reaction means may comprise also a catalyst stripper which is operatively connected to the reaction vessel. A catalyst stripper typically consists of a condenser and a packed column, and is installed typically on top of the reactor. The stripper serves to keep catalyst and excess amounts of the fluorination agent inside the reactor, while allowing product, by-product and HCL to be removed from the reactor as they form.

The reactor and/or stripper may be lined with the fluoropolymer using traditional application techniques such as, for example, spray and bake molding. It has been found, however, that inserting a loose, fluoropolymer liner provides for improved and unexpected results. As used herein, a "loose, fluoropolymer liner" broadly refers to a liner which covers at least portion of metallic part of the reactor and which is fitted from a film or sheet of a fluoropolymer material. Preferably, the sheet has a thickness of no less than about 0.7 mm which is thicker generally than molded liners. As mentioned above, this method of applying the liner is preferred since it tends to produce a less porous lining compared to molding methods like rotary baking. A loose liner is preferred also because it is not limited in thickness and heavy liners may be used. Thicker liners not only lower porosity, but also increase strength. Consequently, a loose, fluoropolymer liner tends to have sufficient strength to span reactor weep holes under reaction pressure. For example, a liner of no less than about 0.7 mm has sufficient strength to span at least a ¼ inch weep hole.

To protect the liner and enhance its reliability, corrosion resistant carbon or silicon carbide brick may be installed in the reactor. These materials are physically more durable than a fluoropolymer liner, and thus are better at resisting abrasion, impact and agitation.

In conducting the reaction, a fluorination agent and a chlorinated organic compound are added to the reactor in the presence of a fluorination catalyst. A halogen exchange then occurs wherein fluorine atoms replace the chlorine atoms of the chlorinated organic compound to produce a desired hydrofluorocarbon.

As used herein, the term "fluorination agent" refers broadly to any suitable material which provides fluorine for the fluorination reaction. A preferred fluorination agent is substantially anhydrous hydrogen fluoride (HF). Any water that is present in the reaction will tend to react with and deactivate the fluorination catalyst. Therefore, substantially anhydrous HF is preferred. The term "substantially anhydrous" as used herein means that the HF contains less than about 0.1 weight % water and preferably contains less than about 0.05 weight % water. It should be understood, however, that the presence of water in the reaction can be compensated for by increasing the amount of catalyst used.

As used herein, the term "chlorinated organic compound" refers broadly to any hydrocarbon having at least one chlorine atom. Suitable chlorinated organic compounds include hydrochlorofluorocarbons (compounds containing carbon, chlorine, fluorine and hydrogen), hydrochlorocarbons (compounds containing carbon, chlorine and hydrogen) and chlorofluorocarbons (compounds containing carbon, chlorine and fluorine) or mixtures thereof. In a preferred embodiment, the chlorinated organic compound has a formula of $C_nH_mF_xCl_y$, wherein $1 \leq n \leq 7$, $0 \leq m \leq 16$, $x \leq 16$, $0 \leq y \leq 16$, and $(m+x+y) \leq (2n+2)$, more preferably, $2 \leq n \leq 5$, $0 \leq m \leq 12$, $1 \leq x \leq 12$, $0 \leq y \leq 12$, and still more preferably, $n=3$, $0 \leq m \leq 8$, $1 \leq x \leq 8$, $0 \leq y \leq 8$.

It should be understood that as the number of carbon atoms in the chlorinated organic compound molecule increases, the temperature at which it decomposes generally decreases. Chlorinated organic compounds having two or more carbons tend to decompose at temperatures near or below their boiling point. For such compounds, it is therefore desirable to maintain and react them in their liquid state.

The term "fluorination catalyst", as used herein, means any inorganic metal catalyst used for the substitution of fluorine for chlorine in the chlorinated organic compound. The fluorination catalysts employed are halides of metals such as, for example, Sb (V), Ta (V), Mo(V), Nb (V), Sn (IV), Ti (IV), Sb(III) and B(III) and mixtures of two or more thereof. Preferred catalysts include $SbCl_5$, $SbF_5$, $SbCl_3$, $TaCl_5$, $SnCl_4$, $NbCl_5$, $TiCl_4$, $MoCl_5$, and mixtures of two or more thereof. Antimony pentachloride is more preferred because of its low cost and availability. The fluorination catalysts used in this invention preferably have a purity of at least about 97%.

The amount of catalyst used can vary widely and can be determined by someone skilled in the art without undue experimentation. The amount depends on a number of factors including the catalyst employed, reactants and other process variables. Although relatively low catalyst concentrations are effective (e.g. less than 0.05 mole per mole organic added), higher quantities (0.1 to 0.5 mole catalyst per mole of organic) may be desirable in order to enhance the reaction rate and consequently improve product output. In a batch process, the more preferred amount of catalyst used is 0.1 to 0.25 mole of catalyst per mole of organic.

The chlorinated organic compound and the fluorination agent are added to the reactor which is preferably charged with a fluorination catalyst. It is preferable for the chlorinated organic compound to be fed into the reactor in liquid phase since hydrochlorocarbons with 2 or more carbons tend to decompose at temperatures near their boiling point. Once the reaction is under way, the starting materials may be added under pressure to supply additional reactants for a continuous process.

The amount of fluorination agent supplied to the reactor should be at least stoichiometric in relation to fluorine to chlorine, e.g., at least about 6 moles HF per mole of $CCl_3 CH_2 CCl_3$ or at least about 8 moles HF per mole of $CCl_3 CH_2 CCl_2$-$CH_2 CCl_3$. Generally, a stoichiometric excess of HF is preferred so that HF essentially acts as a solvent for the fluorination reaction. Excessive amounts of HF, however, limit the output of the product for a batch process. The HF/organic mole ratio is preferably between about 1:1 and about 30:1; more preferably between about 8:1 and about 20:1; most preferably between about 10:1 and about 15:1.

It may be advantageous to periodically regenerate catalyst due to the deactivation of the catalyst over time. For example, if the catalyst is pentavalent, it is preferable to oxidize the catalyst from its trivalent to its more active pentavalent state. This may be accomplished by any means known in the art. When Sb(V) halides are used as the catalyst, chlorine may be co-fed in an amount sufficient to maintain the antimony salts in the +5 oxidation state which generally equates to about 0.06–0.1 lbs chlorine for every pound of $SbCl_5$ catalyst. The chlorine may be continuously added when operating in a continuous mode, or periodically added when operating in a batch mode. One of ordinary skill in the art can readily determine without undue experimentation the amount of chlorine to be added in order to optimize the use of the catalyst.

Preferably, the fluorination agent and chlorinated organic compound starting material are simultaneously fed to the reactor after the reactor reaches desired temperature. The temperature at which the fluorination reaction is conducted and the period of reaction will depend on the starting material and catalyst used. One of ordinary skill in the art can readily optimize the conditions of the reaction without undue experimentation to obtain the desired results. Temperatures will generally range from about 30° to about 200° C., preferably from about 50° to about 150° C., and most preferably from about 70 to about 130° C. To add heat to the reaction, it may be beneficial to superheat the fluorination agent and/or to preheat the chlorinated organic compound feeds. Top catalyst stripper temperature should be maintained such that most of the unreacted fluorination agent and catalyst are refluxed to the reactor which depends upon conditions such as reaction temperature, pressure, type of organics, and type of catalyst.

Reaction pressure can vary and optimal pressures can be determined by someone skilled in the art without undue experimentation. Convenient operating pressure range from about 30 to about 300 psi, preferably from about 60 to about 275 psi, and most preferably from about 70 to about 260 psi.

Reaction times are dependent on several factors including catalyst concentration, the type of catalyst, and the temperature. For a batch process, the progress of the reaction can be monitored conveniently by the increase in pressure due to the formation of by-product HCL. Typical reaction times range from about 1 to about 25 hours, and preferably from about 2 to about 8 hours. For a continuous process, the reaction times ranges from about 1 second to about 5 hours, and, preferably, from about 10 seconds to about 1 hour.

In accordance with this invention, HFCs may be produced in high yields and purity with low reactor corrosion by using a fluoropolymer-lined reactor. In the preferred embodiment, HFCs having 2 or more carbon atoms are produced, and in a more preferred embodiment, HFC propanes are produced. Still a more preferred embodiment produces pentafluoropropane and hexafluoropropane, and the most preferred embodiment produces 1,1,1,3,3-pentafluoropropane 1,1,1,3,3,3-hexafluoropropane, and 3,3,3-trifluoropropene.

EXAMPLES

The following examples are illustrative of the practice of the present invention.

Example 1

This example shows a process for producing a hydrofluorocarbon, specifically 1,1,1,3,3 pentafluoropropane (245fa), using a fluoropolymer-lined reactor, specifically a 2.5 gal lined reactor. The reactor was charged with about 19 lb antimony pentachloride catalyst and about 3 lb of liquid anhydrous HF reactant fluorination agent. The reactor was heated subsequently to about 83° C. Next, the organic feed liquid 1,1,1,3,3-pentachloropropane and additional liquid anhydrous HF were fed continuously to the reactor at 0.18 lb/hr and 0.14 lbs/hr respectively. Both reactants were fed at room temperature. The reactor pressure was adjusted to 150 psig.

To recover the HFC, a catalyst stripper was employed. The catalyst stripper consists of a packed column and a condenser installed atop the reactor to keep catalyst and excess amounts of HF inside the reactor, while removing product, by-product, and HCl from the reactor as they form. The top temperature of the catalyst stripper was maintained at about 29° C. The 245fa exiting the catalyst stripper had a purity of about 95%. The productivity of 245fa was about 0.12 lbs/hr. Corrosion was prevented by using PTFE-lined reactor.

Example 2

This example shows also a process for producing 245fa using a PTFE-lined reactor, but higher quantities of product and under different operating conditions. A 50 gal PTFE-lined reactor was charged with about 350 lbs antimony pentachloride catalyst. Reactor temperature was raised to 95° C. Liquid 1,1,1,3,3-pentachloropropane (HCC-240) preheated to about 90° C. and liquid HF super-heated to 100–150° C. were added to the reactor at the rate of 605 lbs/day and 332 lbs/day, respectively. Additionally, 36 lbs/day of chlorine were continuously fed to the reactor to keep catalyst active. The reactor pressure was maintained at about 150 psig.

From the product stream, the catalyst recovered HFC-245fa, HF, HCl and organic by-products such as 1,3,3-tetrafluoropropene, 1-chloro-3,3,3-trifluoropropene, and 1-chloro-1,3,3,3-tetrafluoropropene. About 21 lbs/hr pure HCl were recovered from the product steam by low temperature distillation. The yield of 245fa was about 90%. Corrosion of the reactor was prevented by using the PTFE-loose liner.

Example 3

This example shows a process for producing HFC-236a using a PTFE-lined reactor. In this example, the conditions and equipment used were the same as in Example 2, except the chlorinated organic compound was changed to 1,1,1,3,3,3-hexachloropropane (HCC-230) and the amount of HF was adjusted to 400 lbs/day. The product steam comprised HCl, 1,1,1,3,3,3-hexafluoropropane (HFC-236fa), 1-chloro-1,1,3,3,3-pentafluoropropane (HCFC-235fa), and 1,1,3,3,3-pentafluoropropene among other components. The latter two components can be recycled to produce more HFC-236a. The overall yield of 236fa was about 90%. Corrosion was again prevented by use of a PTFE-lined reactor.

Example 4

This example illustrates the use of a fluoropolymer loose liner in conducting a reaction in which gaseous reactants are fed to the reaction.

To a 4-gal PTFE-lined reactor, 4.3 lbs antimony pentachloride catalyst and about 15 lbs methylene chloride were charged. The reactor was brought to 110° C. with chlorine feed at about 0.1 lb/hr. Then gaseous anhydrous HF and gaseous methylene chloride were fed to the reactor at 0.4 and 0.9 lbs/hr respectively. Both reactants were vaporized before they reached the reactor. The reactor pressure was maintained at 135 psig. The product therein consisted of trifluoromethane (0.19%), difluoromethane (96%), and chlorofluoromethane (3.6%). The productivity of difluoromethane was about 0.5 lbs/hr. Corrosion was prevented by using a PTFE-lined 4-gal reactor.

Comparative Example

This example compares the corrosion rates of prior art reactor metals to the fluoropolymer-lined reactor of the present invention. Rather than generating corrosion rate data based on actual reactor corrosion, representative coupons of the prior art alloys were used. These coupons were exposed to the same reaction conditions as described in Examples 1–4 above. Coupon thickness was measured before and after each reaction and the difference was calculated. The difference in the coupon thickness was then converted to mils per year (MPY) of corrosion (herein referred to as the "corrosion rate") based upon 8,000 hr/year operation. The corrosion rates for the coupons subjected to the conditions of Examples 1 and 2 are presented in Tables 1 and 2 respectively. The corrosion rates for the coupons subjected to the conditions of Examples 3 and 4 are substantially similar to those presented in Tables 2 and 1 respectively and are not repeated herein.

TABLE 1

Corrosion Rates Under the Conditions of Example 1

| Material | Average MPY |
|---|---|
| Carbon Steel 1018 | 190 |
| Stainless Steel 316 | 130 |
| Monel 400 | 180 |
| Inconel-600 | 210 |
| 20CB3 | 260 |
| Hastelloy C-276 | 180 |

TABLE 2

Corrosion Rates Under the Conditions of Example 2

| Material | Average MPY |
|---|---|
| Carbon Steel | 341 |
| Stainless Steel 316 | 256 |
| Alloy 20 | 652 |
| Incoloy 825 | 662 |
| Inconel 600 | 701 |
| Hastelloy C-276 | 190 |
| Monel 400 | 368 |

These tables indicate very high corrosion rates for metals that were exposed to the same conditions as the present invention's fluoropolymer lined reactor which showed little or no corrosion. Generally, a corrosion rate of more than about 10 mil per year is considered to be unacceptable for commercial use. Therefore, none of the alloys tested is acceptable for commercial use under the reaction conditions of the examples.

What is claimed is:

1. A process for producing a hydrofluorocarbon (HFC) comprising the steps of:
   providing a reactor having a loose, fluoropolymer liner;
   adding a chlorinated organic compound in liquid phase and a fluorination agent to said reactor; and
   reacting at least a portion of said chlorinated organic compound with at least a portion of said fluorination agent to produce said HFC.

2. The process of claim 1, wherein said fluorination agent is hydrogen fluoride, and said chlorinated organic compound has the formula $C_nH_mCl_xF_y$, where $1 \leq n \leq 7$, $0 \leq m \leq 16$, $1 \leq x \leq 16$, $0 \leq y \leq 16$, and $(m+x+y) \leq (2n+2)$, and wherein a stoichiometric excess of said HF is maintained.

3. The process of claim 2, wherein $3 \leq n \leq 5$.

4. The process of claim 1, wherein said fluoropolymer is selected from the group consisting of polytetrafluoroethylene, poly(vinylidene fluoride), ethylene-tetrafluoroethylene polymer, ethylene-hexafluoropropylene polymer, tetrafluoroethylene-hexafluoropropylene polymer, any modified version thereof, and blends of two or more thereof.

5. The process of claim 1, wherein said fluorinating agent is superheated and said chlorinated organic compound is preheated prior to adding to the reactor.

6. The process of claim 5, wherein said fluoropolymer is polytetrafluoroethylene or its modified version.

7. The process of claim 1, wherein said reactor has a physical size of at least 1000 gallons.

8. The process of claim 1, wherein said reactor has at least one weep hole.

* * * * *

UNITED STATES PATENT AND TRADEMARK OFFICE
CERTIFICATE OF CORRECTION

PATENT NO. : 5,902,912
DATED : May 11, 1999
INVENTOR(S) : Tung et al.

It is certified that error appears in the above-identified patent and that said Letters Patent is hereby corrected as shown below:

Column 4, line 27, delete "$0 \leq m \leq 16 \leq x \leq 16$" and substitute therefor -- $0 \leq m \leq 16$, $1 \leq x \leq 16$ --.

Signed and Sealed this

Twenty-ninth Day of August, 2000

Attest:

Q. TODD DICKINSON

*Attesting Officer*     *Director of Patents and Trademarks*